United States Patent [19]

Dürrr et al.

[11] Patent Number: 4,623,378

[45] Date of Patent: Nov. 18, 1986

[54] GAMETOCIDAL PYRIDAZINYLCARBOXYLIC ACID DERIVATIVES

[75] Inventors: Dieter Dürrr, Bottmingen; Hans Tobler, Allschwil, both of Switzerland

[73] Assignee: Ciba-Geigy Corporation, Ardsley, N.Y.

[21] Appl. No.: 637,087

[22] Filed: Aug. 2, 1984

[30] Foreign Application Priority Data

Aug. 10, 1983 [CH] Switzerland .................. 4364/83

[51] Int. Cl.⁴ .................. C07D 237/24; A01N 43/58
[52] U.S. Cl. .................. 71/92; 544/239; 549/417
[58] Field of Search .................. 544/239; 71/92

[56] References Cited

U.S. PATENT DOCUMENTS 4,077,797  3/1978  Fischer .................. 544/241
4,345,934  8/1982  Fujimoto .................. 71/92

FOREIGN PATENT DOCUMENTS 0025498   3/1981  European Pat. Off. .
0037133  10/1981  European Pat. Off. .
0037134  10/1981  European Pat. Off. .
 127313   of 1984 European Pat. Off. .

OTHER PUBLICATIONS

Rohr et al, Chem. Abs., 92, 41973n (1979).

Primary Examiner—Mark L. Berch
Attorney, Agent, or Firm—Edward McC. Roberts; Frederick H. Rabin

[57] ABSTRACT

The invention relates to novel pyridazinylcarboxylic acid derivatives of the formula

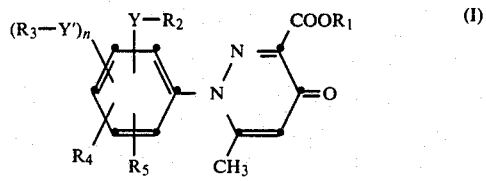

wherein $R_1$ is hydrogen, a cation or $C_1$-$C_6$alkyl, Y and Y' are each independently an oxygen or a sulfur atom or a sulfinyl or sulfonyl group, $R_2$ and $R_3$ are each independently a $C_1$-$C_{12}$alkyl or $C_1$-$C_{12}$alkenyl group which is substituted by one or more halogen atoms, $R_4$ and $R_5$ are each independently hydrogen, halogen, nitro, cyano, $C_1$-$C_6$alkoxy, or $C_1$-$C_6$alkyl which is unsubstituted or substituted by one or more halogen atoms, and n is 0 or 1.

These compounds have gametocidal properties and can be used for influencing generative plant growth and for producing male-sterile plants.

17 Claims, No Drawings

GAMETOCIDAL PYRIDAZINYLCARBOXYLIC ACID DERIVATIVES

The present invention relates to novel pyridazinylcarboxylic acid derivatives with gametocidal properties. The invention also relates to the preparation of the novel compounds and to compositions which contain them. The invention further relates to the use of said compositions and of the compounds contained therein for stimulating generative plant growth, in particular for producing male-sterile plants (use as gametocides), as well as to the use of the pyridazinylcarboxylic acid derivatives for regulating flower formation and the secondary effects associated therewith.

Specifically, the present invention relates to the pyridazinylcarboxylic acid derivatives of the formula I

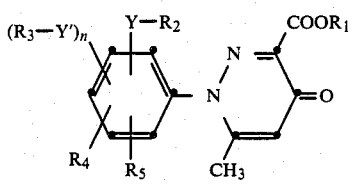

wherein
$R_1$ is hydrogen, a cation or $C_1$–$C_6$ alkyl,
Y and Y' are each independently an oxygen or a sulfur atom or a sulfinyl or sulfonyl group,
$R_2$ and $R_3$ are each independently a $C_1$–$C_{12}$alkyl or $C_1$–$C_{12}$alkenyl group, each substituted by one or more halogen atoms,
$R_4$ and $R_5$ are each independently hydrogen, halogen, nitro, cyano, $C_1$–$C_6$alkoxy, or $C_1$–$C_6$alkyl which is unsubstituted or substituted by one or more halogen atoms, and
n is 0 or 1.

A cation is e.g. the inorganic cation of an element of the first to fourth main group of the Periodic Table. Typical representatives are the alkali metals such as lithium, sodium or potassium, or the alkaline earth metals such as magnesium, calcium, barium, or elements such as aluminium, tin or lead. A cation will also be understood as meaning the cation of an element of the first to eighth auxiliary group, e.g. chromium, manganese, iron, cobalt nickel, copper, zinc, silver or mercury. Preferred are alkali metal and alkline earth metal cations as well as the cations of elements of the third and fourth period of the Periodic Table. The term "cation" also signifies cations such as ammonium ions, hydrazinium ions and guanidinium ions. Examples of suitable ammonium ions are: $NH_4$, $NH(alkyl)_3$, $NH_2(alkyl)_2$ and $NH_3(alkyl)$ such as $NH(CH_3)_3$, $NH(C_2H_5)_3$, $NH_2(CH_3)_2$, $NH_2(C_3H_7$—$n)_2$, $NH_3CH_3$, $NH_3C_4H_9$—n or quaternary ammonium ions such as tetraethylammonium, tetrapropylammonium, tetrabutylammonium, tetrapentylammonium, tetrahexylammonium, tetraheptylammonium, tetraoctylammonium, tetranonylammonium, tetradecylammonium, methyltributylammonium, dimethyldibutylammonium, trimethylbutylammonium, methyltrioctylammonium, benzyltrimethylammonium, benzyltriethylammonium, benzyltripropylammonium, benzyltributylammonium, benzyldimethylhexadecylammonium, benzyldiethylhexadecylammonium, diisobutyl(cresoxyethyl)(dimethylbenzyl)ammonium, trimethylphenylammonium, diphenyldimethylammonium, butyltripropylammonium, tributylphenylammonium or tricaprylmethylammonium. Suitable hydrazinium ions are unsubstituted and substituted hydrazinium compounds, e.g. $NH_2NH_3^\oplus$, $NH_2N(alkyl)_3^\oplus$, $NH_2NH(alkyl)_2^\oplus$, $NH_2NH_2(alkyl)^\oplus$; and examples of guanidinium ions are $NH_2$—$C(=NH)$—$NH_3^\oplus$ or $NH_2$—$NH$—$C(=NH)NH$—$NH_3^\oplus$.

In addition to $NH_4^\oplus$, preferred ammonium cations are in particular those of the type $NH_{(4-a)}$(lower alkyl)$_a^\oplus$, in which $a=1, 2, 3, 4$, and of these, in particular symmetrical tetraalkylammonium ions such as $N(CH_3)_4^\oplus$, $N(C_2H_5)_4^\oplus$, $N(C_4H_{9-n})_4^\oplus$.

Depending on the indicated number of carbon atoms, alkyl by itself or as moiety of another substituent comprises e.g. the following groups: methyl, ethyl, n-propyl, n-butyl, n-pentyl, n-hexyl, n-heptyl, n-octyl, n-nonyl, n-decyl, n-undecyl or n-dodecyl, and the isomers thereof such as isopropyl, isobutyl and tert-butyl.

Within the scope of the indicated number of carbon atoms, alkenyl by itself or as moiety of another substituent comprises all straight chain or branched alkenyl groups such as vinyl, 1-propenyl, allyl, isopropenyl, 2-butenyl or 2-pentenyl.

Halogenated alkyl and alkenyl groups by themselves or as moieties of other substituents may be substituted by one or more identical or different halogen atoms. Preferred alkyl and alkenyl groups are those containing 1 to 6, preferably 1 to 4, carbon atoms and which are substituted by two or more identical halogen atoms. Fluorinated alkyl groups are most preferred.

Examples of halogenated alkyl groups are: $CH_2I$, $CHCl_2$, $CCl_3$, $CH_2Cl$, $CH_2Br$, $CF_2Cl$, $CH_2CH_2CH_2Cl$, $CH_2CF_3$, $CH_2CCl_3$, $CCl_2CHCl_2$, $CH_2CH_2CHCl_2$ and in particular, $CF_3$, $CHF_2$, $CF_2CF_3$, $CF_2CHFCl$ and $CF_2CHF_2$. Examples of halogenated alkenyl groups are: $CH_2CCl=CCl_2$, $CH=CCl_2$ and, preferably, $CCl=CCl_2$ and $CCl=CHCl$.

Halogen by itself or as moiety of another substituent is fluorine, chlorine, bromine or iodine.

Preferred groups of compounds are:
(a) compounds of formula I, wherein $R_1$ is hydrogen, a metal, ammonium or hydrazinium cation or $C_1$–$C_4$alkyl; Y and Y' are each independently an oxygen or a sulfur atom or a sulfinyl or sulfonyl group; $R_2$ and $R_3$ are each independently a $C_1$–$C_{12}$alkyl or $C_1$–$C_{12}$alkenyl group, each substituted by one or more halogen atoms; $R_4$ and $R_5$ are each independently hydrogen, halogen, nitro or $C_1$–$C_6$alkyl and n is 0 or 1; with those compounds being preferred in which $R_1$ is hydrogen, the cation of an alkali metal or alkaline earth metal, the ammonium cation or $C_1$–$C_4$alkyl; Y and Y' are each independently an oxygen or a sulfur atom or a sulfonyl group; $R_2$ and $R_3$ are each independently a $C_1$–$C_3$alkyl group which is substituted by at least two fluorine atoms, or a $C_2$–$C_4$alkenyl group which is substituted by at least two chlorine atoms; $R_4$ is hydrogen, halogen, nitro or $C_1$–$C_4$alkyl; $R_5$ is hydrogen; and n is 0 or 1;
(b) compounds of formula I, wherein $R_1$ is hydrogen, the sodium, potassium, magnesium or ammonium cation or $C_1$–$C_4$alkyl, Y is an oxygen or a sulfur atom or a sulfonyl group; $R_2$ is trifluoromethyl, difluoromethyl, 1,1,2,2,2-pentafluoroethyl, 1,1,2,2-tetrafluoroethyl, 1,2-dichlorovinyl or 1,2,2-trichlorovinyl; Y' is an oxygen atom, $R_3$ is difluoromethyl, $R_4$ is hydrogen, chloro, nitro or methyl, $R_5$ is hydrogen and n is 0 or 1, preferably 0, and the —Y—R$_2$ group is preferably in the 3- or 4-position; with those compounds being preferred in which R$_1$ is hydrogen, the sodium cation, methyl or ethyl; Y is an oxygen or a sulfur atom, R$_2$ is trifluoromethyl, difluoromethyl, 1,1,2,2-tetrafluoroethyl, 1,1,2,2,2-pentafluoroethyl or 1,2-dichlorovinyl; R$_4$ is hydrogen or methyl; R$_5$ is hydrogen and n is 0;

(c) compounds of the formula I, wherein R$_1$ is hydrogen, methyl or ethyl, Y is an oxygen or a sulfur atom, R$_2$ is trifluoromethyl, difluoromethyl, 1,1,2,2-tetrafluoroethyl or 1,1,2,2-pentafluoroethyl, R$_4$ is hydrogen or methyl, R$_5$ is hydrogen, n is 0, and the —Y—R$_2$ group is preferably in the 4-position; with those compounds being preferred in which R$_1$ is hydrogen, methyl or ethyl, Y is an oxygen atom, R$_2$ is trifluoromethyl or difluoromethyl, R$_4$ is hydrogen or methyl, R$_5$ is hydrogen, n is 0, and the —Y—R$_2$ group is preferably in the 4-position.

Preferred individual compounds are:

[1-(4-(1,1,2,2-tetrafluoroethoxy)phenyl)-1,4-dihydro-4-oxo-6-methylpyridazin-3-yl]carboxylic acid,

[1-(3-methyl-4-(1,1,2,2-tetrafluoroethoxy)phenyl)-1,4-dihydro-4-oxo-6-methyl-pyridazin-3-yl]carboxylic acid,

[1-(4-trifluoromethylthio)phenyl)-1,4-dihydro-4-oxo-6-methylpyridazin-3-yl]carboxylic acid,

[1-(4-difluormethylthio)phenyl)-1,4-dihydro-4-oxo-6-methylpyridazin-3-yl]carboxylic acid,

[1-(4-(1,1,2,2,2-pentafluoroethoxy)phenyl)-1,4-dihydro-4-oxo-6-methylpyridazin-3-yl]carboxylic acid and, in particular,

[1-(4-(trifluoromethoxy)phenyl)-1,4-dihydro-4-oxo-6-methylpyridazin-3-yl]carboxylic acid,

[1-(4-(difluoromethoxy)phenyl)-1,4-dihydro-4-oxo-6-methylpyridazin-3-yl]carboxylic acid,

[1-(2-methyl-4-(difluoromethoxy)phenyl)-1,4-dihydro-4-oxo-6-methylpyridazin-3-yl]carboxylic acid, methyl [1-(4-trifluoromethoxy)phenyl)-1,4-dihydro-4-oxo-6-methylpyridazin-3-yl]carboxylate, and ethyl [1-(4-(trifluoromethoxy)phenyl)-1,4-dihydro-4-oxo-6-methylpyridazin-3-yl]carboxylate.

The compounds of formula I are conveniently prepared by rearranging a hydrazone of the formula V

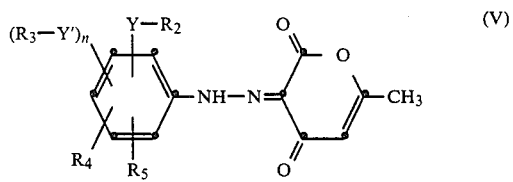

wherein Y, Y', R$_2$, R$_3$, R$_4$, R$_5$ and n are as defined for formula I, by addition of an acid, a base or an amine, to give the pyridazinylcarboxylic acid derivative of the formula I, and, if desired, if R$_1$ in formula I is C$_1$–C$_6$alkyl, converting the compound so obtained into the corresponding alkyl ester.

The rearrangement of a hydrazone of the formula V, wherein Y, Y', R$_2$, R$_3$, R$_4$, R$_5$ and n are as defined for formula I, to give a pyridazinylcarboxylic acid derivative of the formula I, wherein R$_1$ is C$_1$–C$_6$alkyl, can also be effected by transesterification by reacting a hydrazone of the formula V with an alcohol of the formula VI

R$_1'$—OH (VI)

wherein R'$_1$ is C$_1$–C$_6$alkyl, under the conditions described for the rearrangement, said reaction being preferably carried out in anhydrous medium using a desiccant.

The preparation of hydrazones of the formula V and the rearrangement thereof likewise constitute an object of the invention. The process is conveniently carried out by converting an aniline of the formula II

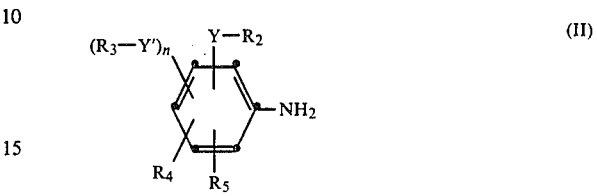

wherein Y, Y', R$_2$, R$_3$, R$_4$, R$_5$ and n are as defined for formula I, into a corresponding diazonium salt of the formula III

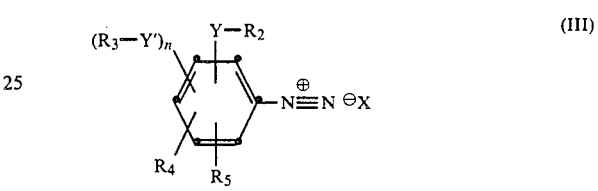

wherein Y, Y', R$_2$, R$_3$, R$_4$, R$_5$ and n are as defined for formula I, and X is a suitable anion, for example a chlorine anion, and reacting said diazonium salt with the pyrone of the formula IV

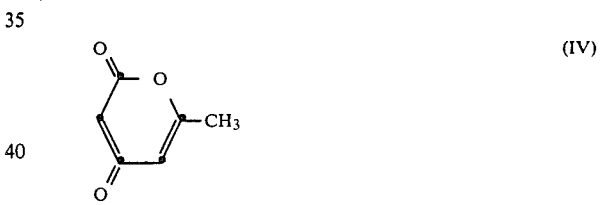

or a salt thereof, and rearranging the resultant hydrazone of the formula V

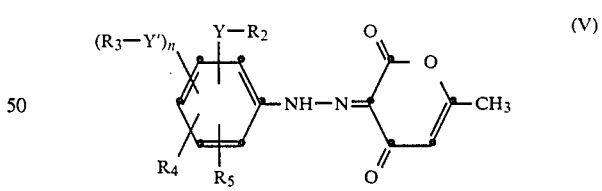

wherein Y, Y', R$_2$, R$_3$, R$_4$, R$_5$ and n are as defined for formula I, by addition of an acid, a base or an amine, optionally by reaction with with an alcohol of the formula VI

R$_1'$—OH (VI)

wherein R'$_1$ is C$_1$–C$_6$alkyl, to give the pyridazinylcarboxylic acid derivative of the formula I, and, if desired, if the rearrangement is not carried out with an alcohol of the formula VI and R$_1$ in formula I is C$_1$–C$_6$alkyl, converting the compound so obtained into the corresponding alkyl ester. It is preferred to carry out the reaction of a hydrazone of the formula V with an alcohol of the formula VI in anhydrous medium and in the presence of a desiccant.

The conversion of the aniline of the formula II into the corresponding diazonium salt of the formula III can be carried out in a manner known per se, for example by reacting an aniline of the formula II with concentrated hydrochloric acid and sodium nitrite.

The reaction of the diazonium salt of the formula III with a pyrone of the formula IV is conveniently carried out in the presence of a polar solvent. Examples of suitable polar solvents are lower alcohols such as methanol, ethanol or isopropanol, dimethylformamide, 1,2-dimethoxyethane or water.

The reaction is normally carried out in the temperature range from $-15°$ to $+60°$ C.

The rearrangement of the hydrazone of the formula V to give the pyridazinylcarboxylic acid derivative of the formula I can be carried out by adding an acid, for example, sulfuric acid, hydrochloric acid, nitric acid, hydrobromic acid, phosphoric acid, trifluoroacetic acid, methanesulfonic acid or perchloric acid, or a base such as sodium or potassium carbonate or sodium or potassium hydroxide, or an amine such as piperidine or morpholine.

The temperature is conveniently in the range from 0° to 150° C., preferably from 40° to 120° C. and, most preferably, from 60° to 100° C.

The rearrangement can be carried out in an inert solvent. Examples of suitable solvents are: halogenated hydrocarbons such as chloroform, carbon tetrachloride, methylene chloride or chlorobenzene, or aromatic hydrocarbons such as benzene, toluene or xylene.

Examples of suitable desiccants for the esterification of a hydrazone of the formula V with an alcohol of the formula VI are: phosphorus pentoxide, a tetra($C_1$-$C_4$)alkyl silicate, a tri($C_1$-$C_4$alkyl)borate, a tri($C_1$-$C_4$alkyl)orthoformate, a $C_1$-$C_4$alkyl ketal, a $C_1$-$C_4$alkyl acetal or a molecular sieve, for example a Linde Type 4-A molecular sieve.

The starting materials are known or they may be prepared by methods analogous to known ones.

Various pyridazine derivatives with plant regulatory properties have been disclosed in U.S. patent specification No. 4,345,934 and in European patent publication Nos. 25.498, 37.133 and 37.134.

Surprisingly, it has now been found that the pyridazinylcarboxylic acid derivatives of formula I and compositions containing them are characterised in particular by their selective influence on plant metabolism. This selective influence on the physiological processes of plant development makes it possible to use the compounds of formula I for different purposes, especially for those in connection with increasing the yield of useful plants and with labour-saving in measures taken in the breeding and production of hybrid seeds.

Previous experience with growth regulators has shown that they are able to induce one or more different responses in the plants to which they are applied. These different responses depend substantially on the time of application, i.e. on the physiological condition of the seed or on the state of development of the plant, the nature of the application, as well as in particular on the concentrations employed. Such responses in turn differ, depending on the species of plant. The application of compounds of the formula I now affords the possibility of influencing plant growth in the desired manner.

It is possible to regulate the generative growth of numerous monocot and dicot plants with the pyridazinylcarboxylic acid derivatives of the formula I and the agrochemical compositions which contain them, such that the vegetative growth of cultivated plants is influenced advantageously in wide ranges of concentration. Very high rates of application may cause phytotoxic effects. The influence on the generative plant growth differs, depending on the crop plant.

An important means of regulating generative growth resides in the particular property of the pyridazinylcarboxylic acid derivatives of this invention to effect a gametocidal response in different cultivated plants, especially when these compounds are applied to monocot plants such as wheat, rye, barley, oats, rice, maize, sorghum and forage grasses; and also in other plants such as sunflowers, tomatoes, flax, leguminosae (soybeans, beans), rape or cotton. This response induces male sterility in the plants without noticeably influencing the fertility of the female flower parts. An increase in the flower shoots and/or the formation of parthenocarpic fruit is simultaneously observed in numerous cultivated plants. Male sterility is observed either in actual male sterility, viz. that the male flower parts are not formed at all or the pollen is sterile, or in a functional sterility in which the male flower parts are formed but are unable to effect pollination. The compounds of formula I are also able to induce protogyny, i.e. female fertile flower parts are formed prematurely, or the growth of male inflorescences is so delayed that cross-pollination with selected pollen can be carried out.

These gametocidal effects can be utilised with particular advantage in breeding and producing hybrid seeds in agriculture. Hybrid seeds are of particular importance for growing useful plants, particularly the principal food plants and for growing ornamentals. Hybrids are usually healthier than pure varieties and produce higher yields than the most productive parent variety.

To obtain hybrid seed, the breeder crosses two or more carefully selected inbreed lines in a procedure which has been worked out experimentally, and obtains in this manner hybrid seeds from which plants of increased growth and yield are grown.

Hybridisation of monoecious maize plants can also be effected in conventional manner, as male and female flower parts are formed at different parts of the plant (diclinous flowers). The anthers which yield pollen form the top of the maize plant, whereas the spadiceous female inflorescence with the silk (stigma plumes) is formed below the centre of the plant. To breed $F_1$ hybrids, it is usual to plant alternating rows of maize plants of the AA and BB varieties or homozygotic lines. In order to ensure that the AA maize does not form any pollen, the AA plants are sterilised manually or mechanically before the male inflorescences fully develop and are then pollinated with pollen of a BB maize variety to form seeds of an AB hybrid ($F_1$) on the AA plants. The required procedure is not only time-consuming and complicated, but results inevitably in damage to the plant and—especially when sterilisation is effected mechanically—in an unwanted diminution in yield of the line/variety acting as female parent (seed plant).

Hybridisation of monoecious plants such as maize can still be carried out in a more or less economical manner by the above described conventional method. However, this procedure is much more difficult to employ for hybridising small grain cereals, especially those having hermaphroditic flowers and which are normally self-pollinating or also cross-pollinating. With these plants the conventional procedure is extremely time-consuming, labour-intensive and uneconomic and, in particular, requires specially trained personnel. It is only possible to breed small grain hybrids if the self-pollination and cross-pollination is completely inhibited in the plant selected as female parent plant. In practice this has to be done by opening each of the tiny flowers prematurely by hand, carefully removing all the anthers, and then protecting the flowers from unwanted cross-pollination.

Yet a further method of hybridisation is employed for some types of cereals, such as wheat, barley, as well as maize and dicots. Cytoplasmic, male-sterile plants are used in this method and cross-pollination is effected. These cytoplasmic sterile plants are often limited to plant lines ("female" parents) which have the same cytoplasma. As a consequence, cytoplasmically inherited weaknesses or defects, e.g. lack of resistance to a specific pathogen or susceptibility to frost and the like, are transferred by this method inevitably to all hybrids originating from this parent line. Moreover, hybridisation using cytoplasmically male-sterile lines, especially in the case of small grain cereals and also crops of dicots, requires complicated steps of more than ordinary difficulty.

Regardless of the method, it is essential for breeding hybrid seeds always to produce male-sterile and female-fertile plants. The use of chemical sterilisation agents (gametocides) affords a simple, practicable and economic solution to the problem of inducing selective male sterility. Pyridazinylcarboxylic acid derivatives of the formula I have very good male-gametocidal properties and are therefore suitable for these and related purposes. When these compounds are used in crops of useful plants, most of the problems which are associated with conventional methods of hybridisation do not arise at all.

In detail, the following procedure may be employed to produce male-sterile plants and thus to obtain hybrid seeds: The two parent plants to be crossed are planted e.g. in alternate rows. The line chosen as seen plant or mother plant is treated, at the start of flower formation but before the formation of the male flower parts, with a compound of the formula I, to give a row of male-sterile but female-fertile parent plants. The other row is untreated and acts as pollen donor. Its male flower parts form fully and yield the pollen for pollinating the mother or seed plant. The seeds produced by the mother plant are the hybrids and can be harvested in conventional manner. The seeds of the male parent plants are harvested separately and used for other purposes.

The above described method of producing male-sterile plants and of obtaining hybrid seeds constitutes an object of the present invention.

In addition, the compounds of the formula I induce still further growth regulating responses, for example a regulation of flower formation at the desired time and, as a consequence thereof, a controlled ripening of seeds and fruit. This kind of flower stimulation is of economic interest especially in connection with those varieties of plants that simultaneously flower and bear fruit. For example, the treatment of avocado or cotton plants with compounds of the formula I may result, on the one hand, in an advantageous increase in the number of inflorescences and, on the other, the flowering and ripening process may be made subject to a controlled rhythm. Not only would it be possible to achieve in this manner an increase in yield, but also a more rational harvesting and thus better marketing of products.

The regulation of flower formation by treating small-grain cereal plants or forage grasses postemergence, but before the emergence of spikes and anthers, with a compound of formula I according to claim 1, is to be particularly mentioned. The treatment of such plants in the $5\frac{1}{2}$ leaf stage is very advantageous.

A further useful variant of the method of the invention comprises treating cultivated plants before the onset of flowering, said plants being in particular sunflowers, cotton plants, marrows, cucumbers, melons, legumes or ornamentals.

In some cases the application of compounds of the formula I induces a marked prolongation of the flowering period, thereby increasing the possibility of pollinating all blossoms. An extension in time of the flowering phase is also desirable for a whole range of ornamental plants, especially flowers.

After numerous different cultivated plants have been treated with compounds of the formula I, a positive influence on the female inflorescences is observed parallel to the male sterilisation. In this manner the number of female flowers per inflorescence or per plant is often increased, as is also the yield. Such responses are often observed in small grain cereals (such as barley), cucumber plants, sunflowers, legumes (such as soya beans), arborescent plants and ornamentals (such as compositae). In some cases, further related growth regulating effects occurs. In addition, a reduced susceptibility to frost and an increased resistance to pathogens in certain varieties of plants can be observed.

Accordingly, the present invention also relates to the use of pyridazinylcarboxylic acid derivatives of the formula I, or of compositions which contain these compounds, for regulating plant growth, in particular for inducing sterility in male flower parts (use as gametocides) and/or for promoting female flower parts and all secondary responses resulting therefrom, e.g. increase in yield, prolongation of the flowering phase, increased flower formation, regulation of fruiting or of the ripening process and the like.

In addition, the invention relates to the preparation of agrochemical compositions, comprising intimately mixing the compound of formula I with one or more substances or groups of substances described herein. The invention further relates to a method of treating plants, which comprises applying thereto compounds of the formula I or novel compositions containing them. The invention also relates to all novel compounds within the scope of formula I, including the process for their preparation as described herein.

For growth regulation, especially for inducing a gametocidal response, the rates of application are in general in the range from 0.05 (even lower for seed treatment) to 12, preferably from 0.1 to 4, most preferably from 0.1 to 2 kg of active ingredient per hectare (a.i./ha). A favourable time of application, especially for cereal crops, is the period after sowing, but still before the appearance of spikes and anthers, i.e. the $5\frac{1}{2}$-leaf stage or the onset of flowering.

If it is desired to increase the number of inflorescences or to prolong the flowering phase, e.g. in sunflowers, cotton plants, marrows, cucumbers, melons, or ornamentals, then an advantageous rate of application is in the range from 0.1 to 4 kg a.i./ha, and application is made conveniently in an early development stage of the plant.

In plants such as soybeans, in which flowers and fruit occur simultaneously, split application is desirable, i.e. application is preferably repeated periodically using lower concentrations. In general, the rates of application depend also on the type of application and, for simple foliar application, are preferably in the range from 0.1 to 4 kg a.i./ha, in split application from 0.1 to 2 kg a.i./ha and for soil (drench) application from 0.1 to 12 kg a.i./ha, depending on the type of soil.

For seed dressing the rate of application is from about 0.02 to 1 kg a.i. per 100 kg of seeds.

The above indicated rates of application and types of application likewise constitute an object of the invention.

The compounds of formula I are normally applied in the form of compositions and can be applied to the crop area or plant to be treated, simultaneously or in succession, with further compounds. These compounds can be both fertilisers or micronutrient donors or other preparations that influence plant growth. They can also be selective herbicides, insecticides, fungicides, bactericides, nematicides, mollusicides or mixtures of several of these preparations, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of the formula I or an agrochemical composition which contains at least one of said compounds, is foliar application. A very selective male sterility can be induced by carrying out this method at the start of flowering. However, the compound of Formula I can also penetrate the plant through the roots via the soil (systemic action) by impregnating the locus of the plant with a liquid composition, or by applying the compounds in solid form to the soil, e.g. in granular form (soil application). The compounds of formula I can also be applied to seeds (coating) by immersing the seeds in a liquid formulation of the active ingredient or by coating them with a solid formulation. In special cases, further types of application are also possible, e.g. selective treatment of the plant stems or buds.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by intimately mixing and/or grinding the compounds of formula I with extenders, e.g. with solvents, solid carriers, and optionally surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine polypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Within the scope of this invention, a 25% aqueous solution of an adduct of 4-tert-octyl phenol polyglycol ether with 8 moles of ethylene oxide (Extravon) is very suitable. Fatty acid esters of polyoxyethylene sorbitan such as polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in "Mc Cutcheon's Detergents and Emulsifiers Annual", MC Publishing Corp. Ridgewood, N.J., 1981; Helmut Stache "Tensid-Taschenbuch" (Handbook of Surfactants) Carl Hanser Verlag, Munich/Vienna, 1981.

The agrochemical compositions usually contain 0.1 to 99%, preferably 0.1 to 95%, of a compound of the formula I, 99,9 to 1%, preferably 99.8 to 5%, of a solid or liquid adjuvant, and 0 to 25%, preferably 0.1 to 25%, of a surfactant.

Whereas commercial products will preferably be formulated as concentrates, the end user will normally employ dilute formulations.

The composition may also contain further auxiliaries such as stabilisers, antifoams, viscosity regulators, binders, tackifiers as well as fertilisers or other active ingredients for obtaining special effects.

Such agrochemical compositions also constitute an object of the present invention.

The invention is illustrated in more detail by the following Examples, without implying any restriction to what is described therein. Parts and percentages are by weight.

EXAMPLE 1

Preparation of [1-(2-methyl-4-(difluoromethoxy)phenyl)-1,4-dihydro-4-oxo-6-methylpyridazin-3-yl]carboxylic acid

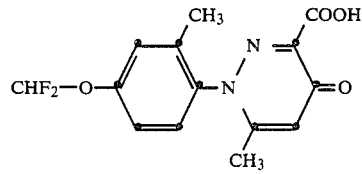

To 69.2 g of 2-methyl-4-(difluoromethoxy)aniline in 100 ml of water are added 160 ml of concentrated hydrochloric acid. With efficient stirring, 56 ml of a 30% solution of sodium nitrite are added dropwise at 0°-5° C. over 1 hour. The clear solution so obtained is added at 0°-5° C. to a solution of 51 g of 4-hydroxy-6-methyl-2-pyrone and 220 g of sodium carbonate in 1.5 liters of water, whereupon a dark yellow precipitate of the diazoniumion pyrone coupling product (m.p. 182°-184° C.) forms. The mixture is stirred for several hours at room temperature, then filtered, and the filter cake is washed with water. The moist filter cake is then stirred at 80° C. in 1 liter of water with 100 g of sodium carbonate until completely dissolved. The [1-(2-methyl-4-(difluoromethoxy)phenyl)-1,4-dihydro-4-oxo-6-methylpyridazin-3-yl]carboxylic acid is precipitated by acidification with concentrated hydrochloric acid, isolated by filtration, dried and recrystallised from ethyl acetate/hexane. Yield: 91.4 g of the title compound with a melting point of 155°-156° C.

EXAMPLE 2

Preparation of [1-(3-methyl-4-(1,1,2,2-tetrafluoroethoxy)phenyl)-1,4-dihydro-4-oxo-6-methylpyridazin-3-yl]carboxylic acid

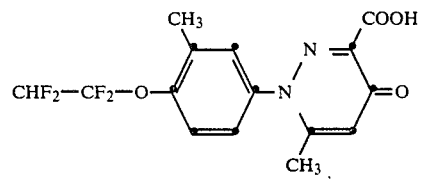

Following the procedure of Example 1, 66.9 g of 3-methyl-4-(1,1,2,2-tetrafluoroethoxy)aniline are diazotised in dilute hydrochloric acid with sodium nitrite and the resultant solution of the diazonium salt is coupled with 4-hydroxy-6-methyl-2-pyrone. The coupling product (m.p. 161°-163° C.) is isolated by filtration and the moist filter cake is added to 1 liter of 20% hydrochloric acid and the mixture is heated under reflux, with stirring. The reaction is complete after 4 hours and the batch is allowed to cool and filtered. The filter cake is dried and recrystallised from ethyl acetate/hexane. Yield: 96.5 g of the title compound with m.p. 170°-172° C.

EXAMPLE 3

Preparation of the sodium salt of [1-(3-methyl-4-(1,1,2,2-tetrafluoroethoxy)phenyl)-1,4-dihydro-4-oxo-6-methylpyridazin-3-yl]carboxylic acid 2.5 g of a 30% solution of sodium methylate in methanol are added to 5 g of [1-(3-methyl-4-(1,1,2,2-tetrafluoroethoxy)phenyl-1,4-dihydro-4-oxo-6-methylpyridazin-3-yl]carboxylic acid in 100 ml of methanol, and the mixture is concentrated by evaporation. The semi-solid residue is taken up in a small amount of methylene chloride and the solution is concentrated by evaporation, affording the above sodium salt (•½$H_2O$) with m.p. >260° C.

EXAMPLE 4

Preparation of methyl[1-(3-methyl-4-(1,1,2,2-tetrafluoroethoxy)phenyl-1,4-dihydro-4-oxo-6-methylpyridazin-3-yl]carboxylate With stirring, 10 ml of concentrated sulfuric acid are added to 10 g of [1-(3-methyl-4-(1,1,2,2-tetrafluoroethoxy)phenyl-1,4-dihydro-4-oxo-6-methylpyridazin-3-yl]carboxylic acid in 50 ml of methanol. The reaction mixture is left to stand for 24 hours, then poured into ice-water, and the product is taken up in chloroform. The chloroform solution is washed twice with a solution of sodium carbonate and then with water until neutral and concentrated. The residue is crystallised by addition of hexane. Yield: 5.5 g of the title ester with m.p. 152°–155° C.

EXAMPLE 5

Preparation of [1-(4-trifluoromethoxy)phenyl-1,4-dihydro-4-oxo-6-methylpyridazin-3-yl]carboxylic acid

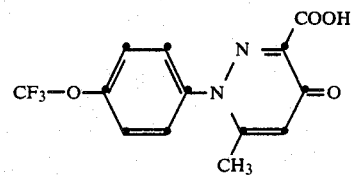

With stirring, 53.1 g of 4-trifluoromethoxyaniline are added to 140 ml of 32% hydrochloric acid in 120 ml of water and the resultant suspension is then cooled. Then 10.5 g of sodium nitrite in 10.5 ml of water are added dropwise at −5° to 0° C. over 30 minutes. After 10 minutes, excess nitrite is destroyed with sulfamic acid. The diazonium solution is added over 10 minutes to a solution of 37.8 g of 4-hydroxy-6-methyl-2-pyrone and 170 g of sodium carbonate in 1.5 liters of water. After 2 hours the precipitate is isolated by filtration, washed with water, and the still moist filter cake is heated under reflux for 4 hours in 770 ml of concentrated hydrochloric acid. The batch is cooled, the product is isolated by filtration, washed with water until neutral, dried and recrystallised from ethyl acetate/hexane, affording 65 g of the title compound with m.p. 192°–194° C.

The following compounds of formula I listed in Table 1 together with the compounds of the foregoing Examples can also be prepared in accordance with one of the methods described above.

TABLE 1

| No. | $R_1$ | Y | $R_2$ | Y' | $R_3$ | $R_4$ | $R_5$ | n | m.p. °C. |
|---|---|---|---|---|---|---|---|---|---|
| 1 | H | 4-O | $CF_3$ | — | — | H | H | 0 | 192–194 |
| 2 | H | 4-O | $CHF_2$ | — | — | H | H | 0 | 161–163 |
| 3 | H | 4-O | $CF_2CHF_2$ | — | — | H | H | 0 | 175–177 |
| 4 | $Na^\oplus$ (.½$H_2O$) | 4-O | $CF_2CHF_2$ | — | — | 3-$CH_3$ | H | 0 | >260 |
| 5 | H | 4-O | $CF_2CHF_2$ | — | — | 3-$CH_3$ | H | 0 | 170–172 |
| 6 | $CH_3$ | 4-O | $CF_2CHF_2$ | — | — | 3-$CH_3$ | H | 0 | 152–155 |
| 7 | H | 3-O | $CF_2CHF_2$ | — | — | H | H | 0 | 178–180 |
| 8 | H | 4-O | $CHF_2$ | — | — | 2-$CH_3$ | H | 0 | 155–156 |
| 9 | $CH_3$ | 4-O | $CF_3$ | — | — | 2-Cl | H | 0 | |
| 10 | $C_2H_5$ | 4-O | $CHF_2$ | — | — | 2-Cl | H | 0 | |
| 11 | $CH_3$ | 3-O | $CHF_2$ | — | — | 4-Cl | H | 0 | |
| 12 | H | 4-O | $CHF_2$ | 2-O | $CHF_2$ | H | H | 1 | |
| 13 | H | 4-S | $CF_3$ | — | — | H | H | 0 | 182–183 |
| 14 | H | 4-S | $CHF_2$ | — | — | H | H | 0 | 212–213 (decompos.) |
| 15 | H | 4-O | $CF_2CF_3$ | — | — | H | H | 0 | 208–209 (decompos.) |
| 16 | H | 4-$SO_2$ | $CF_3$ | — | — | H | H | 0 | |
| 17 | $CH_3$ | 4-O | $CF_3$ | — | — | 3-Cl | H | 0 | |
| 18 | $C_2H_5$ | 4-O | $CHF_2$ | — | — | 3-$NO_2$ | H | 0 | |
| 19 | $CH_3$ | 3-O | $CF_2CHF_2$ | — | — | 4-Cl | H | 0 | |
| 20 | H | 3-O | $CF_3$ | — | — | H | H | 0 | 138–141 |
| 21 | H | 3-O | $CHF_2$ | — | — | H | H | 0 | |
| 22 | H | 3-S | $CF_3$ | — | — | H | H | 0 | |
| 23 | H | 4-O | $CF_3$ | — | — | 2-Cl | H | 0 | |
| 24 | $NH_4^\oplus$ | 4-O | $CHF_2$ | — | — | 2-Cl | H | 0 | |
| 25 | H | 3-O | $CHF_2$ | — | — | 4-Cl | H | 0 | |
| 26 | $C_3H_7$n | 4-O | $CHF_2$ | 2-O | $CHF_2$ | H | H | 1 | |
| 27 | $C_3H_7$iso | 4-S | $CF_3$ | — | — | H | H | 0 | |
| 28 | $C_3H_7$iso | 4-S | $CHF_2$ | — | — | H | H | 0 | |
| 29 | $C_4H_9$n | 4-O | $CF_2CF_3$ | — | — | H | H | 0 | |
| 30 | $Mg^{++}$ | 4-$SO_2$ | $CF_3$ | — | — | H | H | 0 | |
| 31 | H | 4-O | $CF_3$ | — | — | 3-Cl | H | 0 | |
| 32 | $NH_4^\oplus$ | 4-O | $CHF_2$ | — | — | 3-$NO_2$ | H | 0 | |
| 33 | H | 3-O | $CF_2CHF_2$ | — | — | 4-Cl | H | 0 | |
| 34 | $C_3H_7$n | 3-O | $CF_3$ | — | — | H | H | 0 | |
| 35 | $C_3H_7$iso | 3-O | $CHF_2$ | — | — | H | H | 0 | |
| 36 | $C_4H_9$n | 3-S | $CF_3$ | — | — | H | H | 0 | |
| 37 | $K^\oplus$ | 4-O | $CHF_2$ | 2-O | $CHF_2$ | H | H | 1 | |
| 38 | $K^\oplus$ | 3-O | $CF_3$ | — | — | H | H | 0 | |
| 39 | $Na^\oplus$ | 4-O | $CF_3$ | — | — | H | H | 0 | |
| 40 | $K^\oplus$ | 4-O | $CF_3$ | — | — | H | H | 0 | |
| 41 | $NH_4^\oplus$ | 4-O | $CF_3$ | — | — | H | H | 0 | |
| 42 | $CH_3$ | 4-O | $CF_3$ | — | — | H | H | 0 | 136–137 |

TABLE 1-continued

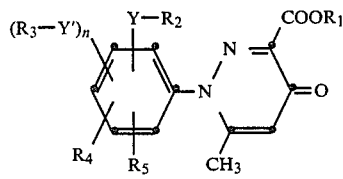

| No. | $R_1$ | Y | $R_2$ | Y' | $R_3$ | $R_4$ | $R_5$ | n | m.p. °C. |
|---|---|---|---|---|---|---|---|---|---|
| 43 | $C_2H_5$ | 4-O | $CF_3$ | — | — | H | H | 0 | 129-130 |
| 44 | H | 4-O | $CCl=CCl_2$ | — | — | H | H | 0 | |
| 45 | H | 4-O | $CCl=CHCl$ | — | — | H | H | 0 | 178-180 |

FORMULATION EXAMPLES

Formulation Examples for liquid active ingredients of the formula I (throughout, percentages are by weight)

| 6. Emulsifiable concentrates | |
|---|---|
| a compound of Table 1 | 25% |
| calcium dodecylbenzenesulfonate | 5% |
| castor oil polyethylene glycol ether (36 moles of ethylene oxide) | 5% |
| tributylphenol polyethylene glycol ether (30 moles of ethylene oxide) | — |
| cyclohexanone | — |
| xylene mixture | 65% |

Emulsions of any required concentration can be produced from such concentrates by dilution with water.

| 7. Solutions | (a) | (b) |
|---|---|---|
| a compound of Table 1 | 80% | 10% |
| ethylene glycol monomethyl ether | 20% | — |
| polyethylene glycol 400 | — | 70% |
| N—methyl-2-pyrrolidone | — | 20% |

These solutions are suitable for application in the form of a microdrops.

| 8. Granulates | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 9. Dusts | (a) | (b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

Formulation examples for solid active ingredients of the formula I (throughout, percentages are by weight)

| 10. Wettable powders | (a) | (b) | (c) |
|---|---|---|---|
| a compound of Table 1 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| 11. Emulsifiable concentrate | |
|---|---|
| a compound of Table 1 | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 12. Dusts | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carriers, and grinding the mixture in a suitable mill.

| 13. Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 14. Coated granulate | |
|---|---|
| a compound of Table 1 | 3% |

-continued

| 14. Coated granulate | |
|---|---|
| polyethylene glycol 200 | 3% |
| kaolin | 94% |

The finely ground active ingredient is uniformly applied, in a mixer, to the kaolin moistened with polyethylene glycol. Non-dusty coated granulates are obtained in this manner.

| 15. Suspension concentrate | |
|---|---|
| a compound of Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water. Formulation assistants which increase the adhesion of the active ingredient to the plant, e.g. mineral or vegetable oils, act very advantageously in foliar application.

BIOLOGICAL EXAMPLES

EXAMPLE 16

Gametocidal activity in small grain cereals (a) Induction of male sterility

Summer wheat is grown in pots measuring 18×18×18 cm in compost-containing soil enriched with fertiliser. The plants are grown at 12° to 15° C. and under short-day (10 hour) conditions. After tillering, the temperature is raised to 18°–24° C. and the plants are moved to long-day conditions (14 hours). The young plants are sprayed to afford preventive or curative protection from aphids and mildew. The plants are sprayed with the test compounds when they have reached the flag leaf stage (stage 7 on Feekes' scale). The spray mixture contains 2000 or 500 ppm of test compound as well as 0.1% of Extravon, and is applied at a rate of application corresponding to 800 l/ha.

After application, but before appearance of the anthers, each spike is covered to protect it from cross-pollination. Evaluation of gametocidal activity is made at maturity by counting the number of seeds formed in each spike. Untreated wheat plants whose spikes have also been covered are used for comparison purposes.

Some results of test (a) are reported in the following table.

TABLE 2

| Concentration, ppm | Gametocidal activity (%) Compound Nr. | | | |
|---|---|---|---|---|
| | 3 | 4 | 5 | 6 | 7 |
| 500 | 100 | 100 | 83.7 | 45.9 | 12.2 |
| 2000 | 100 | 100 | 100 | 100 | 24.6 |

Corresponding results are also obtained in analogous tests with barley and rye.

(b) Fertility test (formation of hybrid seeds)

A control group of wheat plants is treated as in (a) and either kept isolated or with their spikes covered. The spikes of the treated plants are cross-pollinated with pollen of another selected wheat variety. The fertility is evaluated at harvest time by counting the number of hybrid seeds in each spike. Untreated wheat plants and wheat plants which have been treated and with their spikes covered are used for comparison purposes.

Test (b) shows that the fertility of the plants used in test (a) is fully or substantially retained.

EXAMPLE 17

Gametocidal activity in wheat

Summer wheat of the "Sonora" variety is grown in pots measuring 18×18×18 cm in compost-containing soil enriched with fertiliser. The plants are grown at 12° to 15° C. and under short-day (10 hour) conditions.

After tillering, the temperature is raised to 18°–24° C. and the plants are moved to long-day conditions (14 hours). The young plants are sprayed to afford preventive or curative protection from aphids and mildew. When the spike primordia on the main shoot have reached a length of 2 to 3 mm (early application), or a length of 8 to 10 mm (late application), the plants are sprayed uniformly with a spray mixture prepared from a 10% aqueous solution of [1-(4-(trifluoromethoxy)-phenyl)-1,4-dihydro-4-oxo-6-methylpyridazin-3-yl]-carboxylic acid at a rate of application corresponding to 13, 40 and 120 g of a.i./ha. The solution employed as spray mixture contains 16,25 ppm, 50 and 150 ppm of test compound. The spray mixture is applied in a concentration corresponding to 800 l/ha.

After application, but before the appearance of the anthers, each spike of half of the plants is covered to protect it from cross-pollination. Evaluation of gametocidal activity is made at maturity by counting the number of seeds in each spike. Untreated wheat plants whose spikes have been covered and uncovered are used for comparison purposes (control=100%). The results are reported in the following table.

TABLE 3

| | Seeds per spike in percent of controls | | | | | |
|---|---|---|---|---|---|---|
| | covered rate of application g a.i./ha | | | uncovered rate of application g a.i./ha | | |
| Application | 13 | 40 | 120 | 13 | 40 | 120 |
| early | 95 | 0 | 0 | 100 | 69 | 50 |
| late | 0 | 0 | 0 | 49 | 41 | 11 |

EXAMPLE 18

Gametocidal activity in wheat (systemic)

When the spike primordia on the main shoot have reached a length of 2 to 3 mm, summer wheat plants of the "Calanda" variety are treated with a drench formulation prepared from a 10% aqueous solution containing 180 and 540 ppm of test compound, such that 100 ml of solution per running meter are uniformly applied to the rows of plants. The rate of application of the test compounds is 1 kg/ha and 3 kg/ha.

After application, but before appearance of the anthers, each spike of half of the plants is covered to protect it from cross-pollination. Evaluation of gametocidal activity is made at maturity by counting the number of seeds in each spike. Untreated wheat plants whose spikes have been covered and uncovered are used for comparison purposes (control=100%). The results are reported in the following table.

TABLE 4

| | Seeds per spike in percent of controls | | | |
|---|---|---|---|---|
| | covered rate of application kg a.i./ha | | uncovered rate of application kg a.i./ha | |
| Compound | 1 | 3 | 1 | 3 |
| 1 | 6.3 | 0 | 34.4 | 16.0 |
| 2 | 64.7 | 4.4 | 65.8 | 27.8 |

EXAMPLE 19

Gametocidal activity in soybeans (systemic)

Soybean plants of the "MAPLE ARROW" variety are treated after appearance of the first flower buds with a drench formulation prepared from a 10% aqueous solution of test compound (concentration 25, 75 and 225 ppm), such that 1 liter of formulation is uniformly applied to the rows of plants per 1.5 running meters, taking care not to wet the leaves. The test compounds are applied at rates of application of 0.5 kg/ha, 1.5 ka/ha and 4.5 ka/ha. Evaluation of the gametocidal activity is made at harvest time in accordance with the following criteria: number of young green pods per parcel, number of normal pods per parcel and number of seeds in each pod. Untreated soybean plants are used for comparison purposes (controls). The results are reported in the following table.

TABLE 5 number of young green pods/parcel (1.5 m²) = gs/p
number of normal pods/parcel (1.5 m²) = ns/p
number of seeds/pod = s/p

| | | Rate of application in kg a.i./ha | | | |
|---|---|---|---|---|---|
| | Compound | 0.5 | 1.5 | 4.5 | 0 (control) |
| gs/p | 1 | 19 | 27 | 222 | 28 |
| gs/p | 2 | C | 8 | 16 | 28 |
| gs/p | 8 | 15 | 120 | 795 | 28 |
| ns/p | 1 | 629 | 799 | 530 | 814 |
| ns/p | 2 | C | 659 | 540 | 814 |
| ns/p | 8 | 785 | 1007 | 1068 | 814 |
| s/p | 1 | 2.24 | 2.13 | 1.90 | 2.11 |
| s/p | 2 | C | 2.07 | 1.86 | 2.11 |
| s/p | 8 | 2.10 | 1.48 | 0.24 | 2.11 |

C = as untreated controls

EXAMPLE 20

Gametocidal activity in soybeans

Soybean plants of the "MAPLE ARROW" variety are sprayed uniformly a first time after emergence of the first flower buds and a second time 4 weeks after the first application with a spray mixture prepared from a 10% aqueous solution of test compound (concentration: 500, 1500 and 4500 ppm). The rate of application of test compound is 0.2 kg/ha, 0.6 kg/ha and 1.8 kg/ha. Evaluation is made at harvest time. The results are reported in the following table. Only normally developed pods and seeds have been taken into account for calculating the value "seeds/pod".

TABLE 5 number of young green pods/parcel (1.5 m²) = gs/p
number of normal pods/parcel (1.5 m²) = ns/p
number of seeds/pod = s/p

| | | Rate of application in kg a.i./ha | | | |
|---|---|---|---|---|---|
| | Compound | 0.2 | 0.6 | 1.8 | 0 (controls) |
| gs/p | 8 | 27 | 38 | 385 | 31 |
| ns/p | 8 | 709 | 811 | 1548 | 905 |
| s/p | 8 | 2.09 | 1.85 | 0.54 | 2.06 |

EXAMPLE 21

Gametocidal activity in soybeans

Soybeans plants of the "MAPLE ARROW" variety are treated as in Examples 19 and 20 with a solution of test compound in the indicated concentrations. The number of seeds per parcel (1.5 m²) is determined at maturity in percent of the controls (controls=100%). The results are reported in the following tables.

TABLE 7

| | Test procedure as in Example 19 | | |
|---|---|---|---|
| | Rate of application in kg a.i./ha | | |
| Compound | 0.5 | 1.5 | 4.5 |
| 1 | 82 | 99 | 59 |
| 2 | — | 79 | 58 |
| 8 | 96 | 87 | 14 |

—: no evaluation

TABLE 8

| | Test procedure as in Example 20 | | |
|---|---|---|---|
| | Rate of application in kg a.i./ha | | |
| Compound | 0.2 | 0.6 | 1.8 |
| 1 | 100 | 90 | 79 |
| 8 | 79 | 80 | 45 |

EXAMPLE 22

Gametocidal activity in wheat

Summer wheat of the "Sonora" variety is grown in pots measuring 18×18×18 cm in compost-containing soil enriched with fertiliser. The plants are grown at 12° to 15° C. and under short-day (10 hour) conditions.

After tillering, the temperature is raised to 18°-24° C. and the plants are moved to long-day conditions (14 hours). The young plants are sprayed to afford preventive or curative protection from aphids and mildew. When the spike primordia on the main shoot have reached a length of 2 to 3 mm (early application), or a length of 8 to 10 mm (late application), the plants are sprayed uniformly with a mixture prepared from a wettable powder formulation of the test compound at a rate of application corresponding to 16,25 and 50 ppm. The suspension employed as spray mixture is applied in a concentration corresponding to 800 l/ha.

After application, but before appearance of the anthers, each spike is covered to protect it from cross-pollination. Evaluation of gametocidal activity is made at maturity by counting the number of seeds in each spike. Wheat plants whose spikes have been covered and uncovered are used for comparison purposes (control=100%). The results are reported in the following table.

TABLE 9

| | | Seeds per spike in percent of controls | |
|---|---|---|---|
| | | Rate of application in g a.i./ha | |
| Application | Compound | 13 | 40 |
| early | 42 | 0 | — |
| late | 42 | 0 | — |
| early | 43 | 0 | 0 |
| late | 43 | 0 | — |

— = no evaluation

What is claimed is:

1. A pyridazinylcarboxylic acid derivative of the formula I

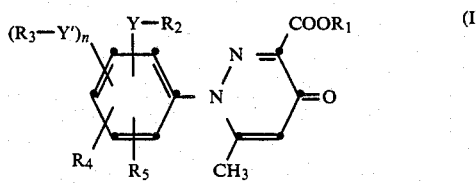

wherein $R_1$ is hydrogen, a agronomically acceptable cation or $C_1-C_6$alkyl,

Y and Y' are each independently an oxygen or a sulfur atom or a sulfinyl or sulfonyl group, $R_2$ and $R_3$ are each independently a $C_1-C_{12}$alkyl or $C_1-C_{12}$alkenyl group, each substituted by one or more halogen atoms, $R_4$ and $R_5$ are each independently hydrogen, halogen, nitro, cyano, $C_1-C_6$alkoxy, or $C_1-C_6$alkyl which is unsubstituted or substituted by one or more halogen atoms, and n is 0 or 1.

2. A pyridazinylcarboxylic acid derivative according to claim 1, wherein $R_1$ is hydrogen, an alkali metal or alkaline earth metal cation, the ammonium cation or $C_1-C_4$alkyl, Y and Y' are each independently an oxygen or a sulfur atom or a sulfonyl group, $R_2$ and $R_3$ are each independently a $C_1-C_3$alkyl group which is substituted by at least two fluorine atoms, or a $C_2-C_4$alkenyl group which is substituted by at least two chlorine atoms, $R_4$ is hydrogen, halogen, nitro or $C_1-C_4$alkyl, $R_5$ is hydrogen, and n is 0 or 1.

3. A pyridazinylcarboxylic acid derivative according to claim 2, wherein $R_1$ is hydrogen, the sodium, potassium, magnesium or ammonium cation or $C_1-C_4$alkyl, Y is an oxygen or a sulfur atom or a sulfonyl group, $R_2$ is trifluoromethyl, difluoromethyl, 1,1,2,2,2-pentafluoroethyl, 1,1,2,2-tetrafluoroethyl, 1,2-dichlorovinyl or 1,2,2-trichlorovinyl, Y' is an oxygen atom, $R_3$ is difluoromethyl, $R_4$ is hydrogen, chloro, nitro or methyl, $R_5$ is hydrogen and n is 0 or 1.

4. A pyridazinylcarboxylic acid derivative according to claim 3, wherein $R_1$ is hydrogen, the sodium cation, methyl or ethyl, Y is an oxygen or a sulfur atom, $R_2$ is trifluoromethyl, difluoromethyl, 1,1,2,2-tetrafluoroethyl, 1,1,2,2,2-pentafluoroethyl or 1,2-dichlorovinyl, $R_4$ is hydrogen or methyl, $R_5$ is hydrogen and n is 0.

5. A pyridazinylcarboxylic acid derivative according to claim 4, wherein $R_1$ is hdrogen, methyl or ethyl, Y is an oxygen or a sulfur atom, $R_2$ is trifluoromethyl, difluoromethyl, 1,1,2,2-tetrafluoroethyl or 1,1,2,2,2-pentafluoroethyl, $R_4$ is hydrogen or methyl, $R_5$ is hydrogen and n is 0.

6. A pyridazinylcarboxylic acid derivative according to claim 5, wherein $R_1$ is hydrogen, methyl or ethyl, Y is an oxygen atom, $R_2$ is trifluoromethyl or difluoromethyl, $R_4$ is hydrogen or methyl, $R_5$ is hydrogen and n is 0.

7. A pyridazinylcarboxylic acid derivative according to claim 5, selcted from the group consisting of

[1-(4-(1,1,2,2-tetrafluoroethoxy)phenyl)-1,4-dihydro-4-oxo-6-methylpyridazin-3-yl]carboxylic acid,

[1-(3-methyl-4-(1,1,2,2-tetrafluoroethoxy)phenyl)-1,4-dihydro-4-oxo-6-methylpyridazin-3-yl]carboxylic acid,

[1-(4-trifluoromethylthio)phenyl)-1,4-dihydro-4-oxo-6-methylpyridazin-3-yl]carboxylic acid,

[1-(4-difluoromethylthio)phenyl)-1,4-dihydro-4-oxo-6-methylpyridazin-3-yl]carboxylic acid,

[1-(4-(1,1,2,2,2-pentafluoroethoxy)phenyl)-1,4-dihydro-4-oxo-6-methylpyridazin-3-yl]carboxylic acid,

[1-(4-(trifluoromethoxy)phenyl)-1,4-dihydro-4-oxo-6-methylpyridazin-3-yl]carboxylic acid,

[1-(4-difluoromethoxy)phenyl)-1,4-dihydro-4-oxo-6-methylpyridazin-3-yl]carboxylic acid,

[1-(2-methyl-4-(difluoromethoxy)phenyl)-1,4-dihydro-4-oxo-6-methylpyridazin-3-yl]carboxylic acid, methyl[1-(4-triflfuoromethoxy)phenyl)-1,4-dihydro-4-oxo-6-methylpyridazin-3-yl]carboxylate, and ethyl[1-(4-(trifluoromethoxy)phenyl)-1,4-dihydro-4-oxo-6-methylpyridazin-3-yl]carboxylate.

8. A gametocidal composition which contains a gametocidally effective amount of a pyridazinylcarboxylic acid derivative of the formula I according to claim 1.

9. A method of regulating flower formation, which comprises treating flowering plants, parts thereof, seeds thereof or the locus thereof, with a compound of the formula I according to claim 1.

10. A method according to claim 9 for producing male-sterile plants which are capable of reproduction.

11. A method according to claim 10, which comprises treating cultivated plants.

12. A method according to claim 11, which comprises treating small grain cereals or forage grasses postemergence, but before the emergence of spikes and anthers.

13. A method according to claim 12, wherein treatment of the plants is carried out in the 5½ leaf stage.

14. A method according to claim 9, wherein the plants are treated before the onset of flowering.

15. A method according to claim 14, wherein the plants treated are sunflowers, cotton plants, marrows, cucumbers, melons, legumes or ornamentals.

16. A method of obtaining hybrid seeds, which comprises inducing male sterilisation in a seed plant selected as female parent plant at the onset of flowering, but before the formation of the male flower parts, by applying a compound of the formula I as claimed in claim 1, subsequently cross-pollinating said plant with pollen of a selected genetically similar plant, and harvesting the ripe hybrid seeds.

17. A method according to claim 16, which comprises applying the compound of formula I to the female parent plants, or to the locus thereof, at a rate of application of 0.05 to 12 kg of active ingredient per hectare.

* * * * *